United States Patent [19]

Newkirk

[11] Patent Number: 5,273,596
[45] Date of Patent: Dec. 28, 1993

[54] NONWOVEN FABRIC FOR DIAPER TOP SHEET AND METHOD OF MAKING THE SAME

[75] Inventor: David D. Newkirk, Greer, S.C.

[73] Assignee: Fiberweb North America, Inc., Simpsonville, S.C.

[21] Appl. No.: 830,745

[22] Filed: Feb. 7, 1992

Related U.S. Application Data

[62] Division of Ser. No. 496,600, Mar. 21, 1990, abandoned.

[51] Int. Cl.⁵ .............................................. B32B 31/16
[52] U.S. Cl. ................................. 156/73.2; 156/73.1; 156/290; 156/308.2; 428/198; 428/171; 428/172; 428/296
[58] Field of Search ..................... 156/73.1, 73.2, 290, 156/308.2; 264/175; 428/198, 296, 171, 172

[56] References Cited

U.S. PATENT DOCUMENTS

| | | |
|---|---|---|
| 3,542,634 | 11/1970 | Such et al. . |
| 3,617,417 | 11/1971 | Olson . |
| 3,692,618 | 9/1972 | Dorschner et al. . |
| 3,737,368 | 6/1973 | Such et al. . |
| 3,956,048 | 5/1976 | Nordgren . |
| 4,041,203 | 8/1977 | Brock et al. . |
| 4,041,951 | 8/1977 | Sanford . |
| 4,216,772 | 8/1980 | Tsuchiya et al. . |
| 4,307,721 | 12/1981 | Tsuchiya et al. . |
| 4,332,253 | 6/1982 | Schoots . |
| 4,377,615 | 3/1983 | Suzuki et al. . |
| 4,391,869 | 7/1983 | Cook et al. . |
| 4,405,297 | 9/1983 | Appel et al. . |
| 4,652,484 | 3/1987 | Shiba et al. . |
| 4,668,566 | 5/1987 | Braun . |
| 4,704,112 | 11/1987 | Suzuki et al. . |
| 4,723,954 | 2/1988 | Pieniak . |
| 4,753,834 | 6/1988 | Braun et al. . |
| 4,798,603 | 1/1989 | Meyer et al. . |

*Primary Examiner*—James J. Bell
*Attorney, Agent, or Firm*—Bell, Seltzer, Park & Gibson

[57] ABSTRACT

A multi-layer, nonwoven fabric useful as an absorbent article top sheet, which is formed of a continuous first layer, comprising hydrophobic thermoplastic fibers, bonded to a second layer, comprising a blend of hydrophobic thermoplastic fibers and natural hydrophilic fibers.

6 Claims, No Drawings

NONWOVEN FABRIC FOR DIAPER TOP SHEET AND METHOD OF MAKING THE SAME

This application is a division of application Ser. No. 07/496,600, filed Mar. 21, 1990, now abandoned.

BACKGROUND OF THE INVENTION

The present invention relates to disposable absorbent pads useful as disposable diapers, adult incontinence pads, sanitary napkins and the like. More particularly, the present invention relates to a nonwoven fabric top sheet for use in such absorbent pads.

Absorbent pads useful as disposable diapers customarily comprise a water-resistant backing sheet, a layer of absorbent or superabsorbent material, and a liquid pervious top sheet (often referred to as a coverstock, or, in diaper applications, a diaper liner) which is placed in contact with the body of the wearer.

To be useful as a top sheet in such a construction, the sheet material should provide fast initial passage of the liquid to be absorbed through the top sheet into the layer of absorbent material (i.e., exhibit a short "strike-through" time), while at the same time delaying or minimizing passage of the absorbed liquids from the layer of absorbent material back through the top sheet to the skin of the wearer (i.e., exhibit high "dryness" or low "surface rewet"). In addition, it is highly desirable that the top sheet material be flexible and soft to the touch. Furthermore, the top sheet material must have sufficient strength not to tear or rupture when wet.

Many different top sheet constructions have been disclosed for the manufacture of such absorbent articles, each typically being claimed to provide an improvement in one or more of the characteristics noted above. In the past, the top sheets typically comprised one or more nonwoven webs of natural or synthetic textile fibers such as rayon, polyamide, polyester, polypropylene, or the like, which were stabilized and secured together by a cured binder composition included within the webs. For example, U.S. Pat. No. 4,332,253 (Schoots) discloses such a top sheet wherein the nonwoven webs are stabilized and secured together with a polymeric binder composition containing at least 1% by weight of combined 2-ethyl hexyl acrylate. The inclusion of the 2-ethyl hexyl acrylate reportedly improves the dryness of the top sheet.

Similarly, U.S. Pat. No. 4,377,615 (Suzuki et al.) discloses a two-layer top sheet in which the nonwoven webs are stabilized and adhered together by an adhesive binder composition. The upper layer of the top sheet containing, as a principal element thereof, hydrophobic fibers and the lower layer containing a mixture of hydrophobic fibers and hydrophilic fibers, with the fibers in the lower layer being of coarser denier than the fibers in the upper layer, and the lower layer containing a smaller amount of the adhesive bonding material than the upper layer. This construction reportedly provides a top sheet exhibiting superior strike- through and dryness properties, an upper layer which is excellent in smoothness, touch and strength, and a lower layer which is excellent in bulkiness and cushion.

Currently, however, most top sheets are thin, low basis weight, carded or spunbond nonwoven fabrics formed by thermally bonding together synthetic thermoplastic fibers that have been made somewhat hydrophilic by the addition of wetting agents. In this regard, U.S. Pat. No. 4,668,566 (Braun) discloses a two-layer top sheet comprising a first layer of polypropylene fibers thermally bonded to a second layer of polyethylene fibers, at discrete locations, which is formed by passing the layers between heated rolls, one having a smooth surface and one having a raised pattern thereon. Reportedly, a top sheet made in this manner exhibits increased softness and tensile strength. However, in order to obtain good strike-through, the polyethylene filaments must be coated with a wetting agent to increase their hydrophilicity.

Similarly, U.S. Pat. No. 4,704,112 (Suzuki et al.) discloses a two-layer top sheet comprising a first layer, having a pattern of apertures, composed of hydrophobic fibers in an amount of 70 to 100% by weight and hydrophilic fibers in an amount of 0 to 30% by weight, thermally bonded to a second layer, having no apertures, composed of hydrophilic fibers in an amount of 50 to 100% by weight and hydrophobic fibers in an amount of 0 to 50% by weight. Useful hydrophobic fibers are said to include polyester, polypropylene, polyethylene, acryl and polyurethane fibers, and useful hydrophilic fibers are said to include rayon fibers, cotton fibers and synthetic fibers such a polyester in which the fiber surface has been imparted with a hydrophilic nature. Reportedly, such a top sheet construction provides an improvement in the balance achieved between surface rewet and strike-through characteristics.

Although the top sheet constructions referred to above indicate that significant advances have been made in the formulation of top sheets exhibiting the desired characteristics, there remain significant disadvantages associated with each of these constructions. For example, the adhesive binder compositions included within the adhesively bonded constructions increase the cost of the top sheet. Additionally, since these binder resin compositions are often applied in the form of aqueous dispersions, the energy required for drying the nonwoven webs and curing the binder resin further increases the cost of manufacture. Moreover, while the thermally bonded constructions avoid the disadvantages associated with the use of adhesive binder resins, they undesirably require the use of hydrophobic thermoplastic fibers which introduce at least three disadvantages. First, the hydrophobic thermoplastic fibers must be treated with wetting agents to provide sufficient hydrophilicity to achieve adequate strike-through. Second synthetic thermoplastic fibers are often judged to provide less comfort than natural hydrophilic fibers. Third, the hydrophobic thermoplastic fibers are not biodegradable, and, thus, contribute to the growing environmental problems of waste disposal and management.

It is, therefore, an object of the present invention to provide a thermally bonded nonwoven top sheet that provides a superior balance of strike-through and dryness properties, and which comprises a significant proportion of natural, biodegradable, hydrophilic fibers.

SUMMARY OF THE INVENTION

The present invention provides a multi-layer, nonwoven fabric ideally suited for use as a top sheet in absorbent articles such as disposable diapers and the like. The fabric comprises a continuous first layer, comprising at least about 75 weight percent hydrophobic thermoplastic fibers, and a second layer, comprising a blend of from about 20 to about 70 weight percent hydrophobic thermoplastic fibers and from about 30 to about 80 weight percent natural hydrophilic fibers. The layers are secured together by bonds formed of melt-fused portions of the hydrophobic thermoplastic fibers.

The unique multi-layer construction of the present invention provides a flexible, comfortable fabric having a smooth soft surface for application against the body, a superior balance of strike-through and surface rewet properties, and sufficient tensile strength to be puncture and tear resistant even when wet. Furthermore, all of these desirable attributes of the fabric have been obtained with the inclusion of a significant proportion of natural, biodegradable, hydrophilic fibers, and without the inclusion of binder resins to stabilize and secure the layers together.

Moreover, with respect to the balance of strike-through and surface rewet properties, Applicant unexpectedly discovered that the multi-layer construction of the invention exhibits a superior balance of strike-through and surface rewet properties in comparison to a single-layer, thermally bonded fabric having about the same overall ratio of hydrophobic fibers to natural hydrophilic fibers, but composed of a homogeneous blend of the hydrophobic and natural hydrophilic fibers. While the reasons for the improvement in both of these properties is not precisely known, it is apparent that the superior balance of these properties exhibited by the multi-layer construction results from the difference in the compositions of the respective layers. Accordingly, it is believed that the first layer must be composed of at least about 75 weight percent hydrophobic thermoplastic fibers, and the second layer must be composed of a blend of hydrophobic thermoplastic fibers and natural hydrophilic fibers wherein the natural hydrophilic fibers account for at least about 30 weight percent of the layer, in order to provide the resulting fabric with this unexpectedly superior balance of short strike-through times and low surface rewet characteristics. Furthermore, the fibrous blend of the second layer must be composed of at least about 20 weight percent hydrophobic thermoplastic fibers in order to provide the resulting thermally bonded fabric with sufficient strength to be useful as a top sheet.

To obtain a top sheet of the invention exhibiting an even better balance of strength, strike-through and surface rewet properties, it is generally preferred that the first layer be composed of at least about 95% by weight hydrophobic thermoplastic fibers, and the second layer be composed of a blend having a weight ratio of thermoplastic hydrophobic fibers to natural hydrophilic fibers in the range of from about 25:75 to about 50:50. In this regard, it is even more preferred for the first layer to be about 100 percent hydrophobic thermoplastic fibers.

DESCRIPTION OF THE PREFERRED EMBODIMENTS

The multi-layer, nonwoven fabric of the invention may be formed in a relatively simple and economical manner by a method comprising the steps of:

(a) forming a first, continuous, nonwoven, fibrous web comprising at least about 75 weight percent hydrophobic thermoplastic fibers;

(b) forming a second, nonwoven, fibrous web comprising a blend of from about 20 to about 70 weight percent hydrophobic thermoplastic fibers and from about 30 to about 80 weight percent natural hydrophilic fibers;

(c) forming a composite web by arranging the first and second webs in an overlying adjacent relationship;

(d) thermally bonding the first and second nonwoven webs together by causing melt-fusing of the hydrophobic thermoplastic fibers; and (e) allowing the composite web to cool to resolidify the melt-fuse thermoplastic fibers and strengthen the bonds formed between the layers.

The nonwoven webs formed in steps (a) and (b) of the above recited method may be prepared from staple fibers by conventional means such as air laying and carding techniques. Alternatively, when the web formed in step (a) consists entirely of hydrophobic thermoplastic fibers, it can be formed from continuous hydrophobic thermoplastic fibers by the spunbond process. Webs formed from continuous thermoplastic fibers by the spunbond process are well known in the art as disclosed in U.S. Pat. Nos. 3,692,618; 4,041,203; 4,405,297 and 4,753,834, the disclosures of which are incorporated herein by reference.

The fibers used in the nonwoven webs formed in steps (a) and (b) are preferably of a size ranging from about 1 to 6 denier, more preferably from about 1 to 3 denier, with the most preferred fibers ranging in size from about 1.5 to 2.5 denier. Typically, the smaller the fiber the softer the resulting fabric will be to the touch. In this respect, the use of fibers of greater than about 6 denier is not preferred in absorbent article top sheets as such fibers undesirably decrease the softness of the resulting fabric to a level which may cause skin irritation during use.

Hydrophobic thermoplastic fibers useful in the first an second layers of the invention may be formed of hydrophobic thermoplastic materials such as nylon 6, nylon 6.6, polyester, polyethylene, polypropylene and the like. However, polyethylene and polypropylene are generally preferred because of the lower melting points of these materials. Moreover, to be useful in the formation of the top sheet of the invention, these hydrophobic thermoplastic fibers are typically coated with spin finish which contains lubricants, antistats and wetting agents. The wetting agents facilitate the initial strike-through of liquids through the top sheet. Thermobondable polypropylene fibers particularly useful as the hydrophobic thermoplastic fibers of the invention are commercially available from AMOCO Fabrics and Fibers Co. of Atlanta, Ga. and Hercules Inc. of Oxford, Ga. in 1.8 denier and 2.2 denier sizes, respectively.

In addition to single component hydrophobic thermoplastic fibers, bi-component fibers made from two hydrophobic thermoplastic materials of different melting points can also be used in the present invention. Sheath/Core, side-by-side, and other types of bi-component fibers can be used. However, the preferred bi-component fibers are selected from the group consisting of sheath/core fibers of the following resin combinations: polyethylene/polypropylene, polyethylene/polyester, polypropylene/polyester, and copolyester/polyester. Specific examples of such fibers are 1.7 and 3 denier polyethylene/polyester sheath/core fibers available from BASF CORPORATION as Products 1051 and 1050, respectively; 2 and 3 denier copolyester/polyester sheath/core fibers available from CELANESE FIBERS as Type 354; and 1.5 and 3 denier polyethylene/polypropylene sheath/core fibers available from CHORI AMERICA as Dalwabo NBF Type H. Such bi-component fibers may be particularly useful to provide the requisite strength t the top sheet of this invention when the total basis weight of the top sheet is reduced and the total quantity of natural hydrophilic fiber is maximized.

Furthermore, the hydrophobic thermoplastic fiber component of each of these layers may be made up of fibers of a single composition, or a blend of fibers of different compositions, which may or may not be the same for each of the layers. However, it is generally preferred that the hydrophobic thermoplastic fiber components of both layers be formed of fibers of a single composition. In this regard, it is generally most preferred that the hydrophobic thermoplastic fibers in both layers be polypropylene fibers.

Similarly, the natural hydrophilic fiber component of the second layer may be formed of fibers of a single composition or of a blend of fibers of different compositions. Natural hydrophilic fibers useful in the present invention include silk, wool, natural cellulosic fibers such as cotton or wood pulp, and manufactured fibers composed of regenerated cellulose such as rayon and acetate. Preferably, the hydrophilic fibers of the second layer are of a single composition selected from cotton or rayon.

The fabric of the invention preferably has a basis weight within the range of from about 10 to about 30 grams per square yard (g/yd$^2$). At basis weights below about 10 g/yd$^2$, the fabric typically lacks sufficient strength, especially when wet, to be useful as a top sheet in an absorbent article. Furthermore, at such basis weights, containment of the finely divided particles of superabsorbent materials typically used in such absorbent articles becomes a problem, as the particles of absorbent material migrate through the top sheet and escape. At basis weights above about 30 g/yd$^2$, the cost of the fabric generally makes its use in such absorbent articles economically infeasible.

In addition to the basis weight of the fabric, the overall proportion of natural hydrophilic fibers to hydrophobic thermoplastic fibers in the fabric is somewhat limited by the strength requirements of an absorbent article top sheet. In this respect, it is preferred that the fabric have an overall weight ratio of hydrophobic thermoplastic fibers to natural hydrophilic fibers in the range of from about 30:70 to about 70:30, and more preferred in the range of from about 40:60 to about 60:40. In this respect, it is most preferred that the overall weight ratio of hydrophobic thermoplastic fibers to natural hydrophilic fibers be within the range of from about 60:40 to about 50:50. At weight ratios less than about 30:70, the resulting fabric may not have sufficient strength to be useful as an absorbent article top sheet, whereas, at weight ratios above about 70:30, the resulting fabric may contain an insufficient quantity of natural hydrophilic fiber to provide the comfort promised by the inclusion of these fibers or to provide a significant reduction in the non-biodegradable waste generated by such top sheets.

Thermal bonding of the nonwoven webs can be accomplished by any method known in the art which generates melt-bonded thermoplastic filaments. For example, suitable bonding methods include calendering, through air bonding, infrared bonding and ultrasonic bonding techniques. Preferably, however, the webs are bonded together at plurality of discrete regions by calendering the composite web between opposed rolls, wherein the surface of at least one of the rolls is heated to a temperature above the softening point of the hydrophobic thermoplastic fibers. Suitable calendering arrangements for forming this plurality of discrete bonded regions include calendering between a smooth surfaced roll and a roll having a raised pattern on the surface thereof, or between helically engraved rolls as disclosed in U.S. Pat. No. 3,542,634, incorporated herein by reference.

The present invention is further illustrated by the following nonlimiting examples wherein all parts and percentages are by weight unless otherwise indicated.

ILLUSTRATIVE EXAMPLES

EXAMPLE 1

A carded web having a basis weight of approximately 13 g/yd$^2$ and composed of a substantially homogeneous blend of 75 weight percent, 1.5 denier per filament (dpf) rayon staple fiber (commercially available from B.A.S.F. Co. under the trade designation BASF 8171), and 25 weight percent, 2.2 dpf polypropylene staple fiber (commercially available from Hercules Co. under the trade designation T185) was laid on a moving belt. This layer was overlaid with a carded web having a basis weight of approximately 8 g/yd$^2$ and consisting of 100 percent of the same 2.2 dpf polypropylene staple fiber used in the other layer. The two-layered assembly, having an overall weight ratio of polypropylene to rayon of 56:44, was then bonded via calendering between a smooth surfaced steel roll maintained at 296° F. and a steel roll having a raised pattern on its surface and maintained at 300° F. The rolls were compressed together under a pressure of 150 pounds per linear inch (pli), and the web was passed between the rolls at a speed of 200 feet per minute.

EXAMPLE 2

A carded web having a basis weight of approximately 16.5 g/yd$^2$ and composed of a substantially homogeneous blend of 75 weight percent of the 1.5 dpf rayon staple fiber used in Example 1 and 25 weight percent of the 2.2 dpf polypropylene staple fiber used in Example 1 was laid on a moving belt. This layer was overlaid with a carded web having a basis weight of approximately 9.5 g/yd$^2$ and consisting of 100 percent of the 2.2 dpf polypropylene staple fiber used in Example 1. The two-layered assembly, having an overall weight ratio of polypropylene to rayon of 56:44, was then bonded via calendering between a smooth surfaced steel roll maintained at 330° F. and a steel roll having a raised pattern on its surface and maintained a 302° F. The rolls were compressed together under a pressure of 150 pli, and the web was passed between the rolls at a speed of 200 feet per minute.

EXAMPLE 3

A carded web having a basis weight of approximately 14.5 g/yd$^2$ and composed of a substantially homogeneous blend of 75 weight percent, 1.5 dpf rayon staple fiber (commercially available from B.A.S.F. Co. under the trade designation BASF 8174), and 25 weight percent of the 2.2 dpf polypropylene staple fiber used in Example 1 was laid on a moving belt. This layer was overlaid with a carded web having a basis weight of approximately 13.5 g/yd$^2$ and consisting of 100 percent of the 2.2 dpf polypropylene staple fiber used in Example 1. The two-layered assembly, had an overall weight ratio of polypropylene to rayon of 61:39, and was bonded as described in Example 2.

EXAMPLE 4

A two-layered assembly, having an overall weight ratio of polypropylene fibers to rayon fibers of 61:39, prepared as described above in Example 3, was bonded via passing the web between a first pair of rolls consisting of a smooth surfaced steel roll maintained at 331° F. and a steel roll having a raised pattern on its surface and maintained at 301° F., and then passing the web between a second pair of rolls consisting of a smooth surfaced steel roll maintained at 304° F. and a steel roll having a raised pattern on its surface and maintained at 330° F. The rolls in both sets were compressed together under a pressure of 150 pli, and the web was passed between the rolls at a speed of 200 feet per minute.

CONTROL EXAMPLE A

A carded web having a basis weight of approximately 13 g/yd$^2$ and composed of a substantially homogeneous blend of 50 weight percent of the 1.5 dpf rayon staple fiber used in Example 1 and 50 weight percent of the 2.2 dpf polypropylene staple fiber used in Example 1 was laid on a moving belt. This layer was overlaid with an identical carded web to form a two-layered assembly, having an overall weight ratio of polypropylene fibers to rayon fibers of 50:50. The two-layered assembly was bonded via calendering between a smooth surfaced steel roll maintained at 315° F. and a steel roll having a raised pattern on its surface and maintained at 286° F. The rolls were compressed together under a pressure of 150 pli, and the web was passed between the rolls at a speed of 180 feet per minute.

The strip tensile strength, caliper, strike-through, surface rewet and absorption capacity properties of the samples prepared in the foregoing Examples were tested according to the procedures outlined below.

Strip Tensile Strength

Strip tensile strength was evaluated by breaking a one inch by seven inch long sample generally following ASTM D1682-64, the One-Inch Cut Strip Test. The instrument cross-head speed was set at 5 inches per minute and the gauge length was set at 5 inches. The tensile strength in both the machine direction ("MD") and the cross direction ("CD") was evaluated. The strip tensile strength or breaking load, reported in grams per inch, is the average of at least eight measurements.

Caliper (Under Compression)

Caliper was determined by measuring the distance between the top and the bottom surface of the sheet while the sheet was held under a compression loading of 10 grams per square yard. The result, reported in mils, is the average of ten measurements.

Strike-Through

Strike-through was evaluated by a method similar to that described in U.S. Pat. Nos. 4,391,869 and 4,041,951, incorporated herein by reference. Strike-through was measured as the time for 5 ml of synthetic urine solution, placed in the cavity of the strike-through plate, to pass through the sample fabric into an absorbent pad. The result, reported in seconds, is generally the average of four tests.

Surface Rewet

Surface rewet was evaluated by a method similar to that described in U.S. Pat. Nos. 4,041,951 and 4,391,869, incorporated herein by reference. Surface rewet, reported in grams, was evaluated by adding synthetic urine through the sample fabric into the absorbent pad until the absorbent pad was nearly saturated. Thus, the sample fabric was wet at the beginning of the surface wetness test. For results denoted as Surface Rewet A, the loading factor was slightly less than 4 grams of synthetic urine per gram of absorbent sample. A uniform pressure loading of 0.5 psi was then applied and the procedure concluded as disclosed in the above patents. For results denoted as Surface Rewet B, the loading factor was increased to slightly over 4 grams of synthetic urine per gram of absorbent sample so that the absorbent pad was saturated with synthetic urine. A uniform pressure loading of 1.0 psi was then applied and the procedure concluded as disclosed in the above patents. The result, reported in grams, is generally the average of four tests.

Absorption Capacity

Absorption capacity was evaluated by measuring the amount of water absorbed by a loosely rolled fabric sample in a specified period of time. Rectangular specimens measuring 3 inches wide and having a length in the machine direction sufficient to yield a sample weight of about 5 grams were cut from the fabric samples to be tested. Each specimen was weighed, rolled into a loose roll and placed in a cylindrical wire basket having a 5 cm. diameter and a length of 8 cm., with the 3 inch edge of the specimen parallel to the side of the basket. The basket was then weighed to determine the combined weight of the specimen and basket. The basket was then dropped into a container of distilled water from a height of 1 inch. After the basket had been submerged for 10 seconds, the basket as removed from the container and allowed to drain for 10 seconds. The container was then weighed again to determine the amount of water absorbed. The absorption capacity is reported as a percentage of the dry weight of the specimen. The result reported is generally the average of five tests.

The results of these tests are shown in Table I. As can be seen from the test results, the samples of the present invention prepared in Examples 1–4 had shorter strike-through times and lower amounts of surface rewet than the homogeneously blended sample of Control Example A. Furthermore, the samples of Examples 1, 3 and 4 each had a lower absorption capacity than the sample of Control Example A. This is an advantageous characteristic for a top sheet material since it is desired that the liquid to be absorbed pass through the top sheet and be absorbed in the layer of absorbent or superabsorbent material below.

TABLE I

| SAMPLE | BASIS WEIGHT (g/yd²) | STRIP TENSILE PROPERTIES (WET) | | CALIPER (MILS) (UNDER COMPRESSION OF 10 g/yd²) | STRIKE-THROUGH (1) (SEC) | | SURFACE REWET (1) | | | | ABSORPTION CAPACITY (%) |
|---|---|---|---|---|---|---|---|---|---|---|---|
| | | | | | | | A 0.5 PSI COMPRESSION | | B 1.0 PSI COMPRESSION | | |
| | | MD (g/in) | CD (g/in) | | UPSIDE | DOWNSIDE | UPSIDE | DOWNSIDE | UPSIDE | DOWNSIDE | |
| EXAMPLE 1 | 21 | 604 | 172 | 9.5 | 1.7 | 1.9 | 0.6 | 0.6 | 2.2 | 2.2 | 994 |
| EXAMPLE 2 | 26 | 601 | 270 | 11.4 | 1.5 | 1.8 | 1.8 | 0.7 | 3.4 | 2.7 | 1039 |
| EXAMPLE 3 | 28 | 894 | 418 | 12.2 | 1.6 | 1.6 | 0.2 | 0.2 | 1.9 | 1.9 | 910 |
| EXAMPLE 4 | 26 | 612 | 190 | 8.9 | 2.2 | 2.0 | 2.1 | 2.0 | 3.5 | 3.3 | 700 |
| CONTROL EXAMPLE A | 26 | 1250 | 307 | 9.0 | 2.7 | 2.7 | 2.9 | 3.0 | 4.0 | 4.1 | 1022 |

(1) FOR THE SAMPLES OF EXAMPLES 1–4 THE UPSIDE IS THE SIDE CORRESPONDING TO THE 100% POLYPROPYLENE LAYER AND THE DOWNSIDE IS THE SIDE CORRESPONDING TO THE RAYON/POLYPROPYLENE BLEND.

What is claimed is:

1. A method of making a multi-layer, non-woven fabric comprising the steps of:
    (a) forming a first, contiguous, nonwoven, fibrous web comprising at least about 75 weight percent hydrophobic thermoplastic fibers;
    (b) forming a second, nonwoven, fibrous web comprising a blend of from about 20 to about 70 weight percent hydrophobic thermoplastic fibers and from about 30 to about 80 weight percent natural hydrophilic fibers;
    (c) forming a composite web by arranging said first and second webs in an overlying adjacent relationship;
    (d) thermally bonding said first and second nonwoven webs together by causing melt-fusing of said hydrophobic thermoplastic fibers; and
    (e) allowing said composite web to cool to resolidify the melt-fused thermoplastic fibers and strengthen the bonds formed between said layers.

2. A method as recited in claim 1, wherein said first and second nonwoven webs are thermally bonded together by a method selected from the group consisting of calendering, through air bonding, infrared bonding and ultrasonic bonding techniques.

3. A method as recited in claim 1 wherein said first and second nonwoven webs are thermally bonded together in a plurality of discrete areas by calendering said composite web between a smooth surfaced roll and a roll having a raised pattern of the surface thereof, wherein the surface of at least one of said rolls is heated to a temperature above the softening point of said hydrophobic thermoplastic fibers.

4. A method as recited in claim 3 wherein said first nonwoven web consists essentially of said hydrophobic thermoplastic fibers and said second nonwoven web consists essentially of a blend of from about 2 to about 50 weight percent hydrophobic thermoplastic fibers and from about 50 to about 75 weight percent natural hydrophilic fibers.

5. A method as recited in claim 4 wherein said hydrophobic thermoplastic fibers in said first and second nonwoven webs are independently selected from the group consisting of nylon fibers, polyester fibers, polyethylene fibers, polypropylene fibers, polyethylene/polyester bi-component fibers, polypropylene/polyester bi-component fibers, polyethylene/polypropylene bi-component fibers, copolyester/polyester bi-component fibers and mixtures thereof; and said natural hydrophilic fibers are selected from the group consisting of acetate fibers, wool fibers, cotton fibers, rayon fibers, silk fibers, wood pulp and mixtures thereof.

6. A method as recited in claim 4 wherein said hydrophobic thermoplastic fibers are polypropylene fibers and said natural hydrophilic fibers are rayon fibers.

* * * * *

UNITED STATES PATENT AND TRADEMARK OFFICE
CERTIFICATE OF CORRECTION

PATENT NO.   : 5,273,596
DATED        : December 28, 1993
INVENTOR(S)  : David D. Newkirk It is certified that error appears in the above-indentified patent and that said Letters Patent is hereby corrected as shown below:

Column 4, line 67, "t" should be -- to --.
Column 10, line 28, "2" should be -- 25 --.

Signed and Sealed this

Seventh Day of June, 1994

Attest:

BRUCE LEHMAN

*Attesting Officer*   *Commissioner of Patents and Trademarks*